(12) United States Patent
Lindsay

(10) Patent No.: US 10,710,038 B2
(45) Date of Patent: Jul. 14, 2020

(54) WATERLESS DECARBOXYLATION

(71) Applicant: Ardent LLC, Roslindale, MA (US)

(72) Inventor: Shanel A. Lindsay, Roslindale, MA (US)

(73) Assignee: Ardent LLC, Roslindale, MA (US)

( * ) Notice: Subject to any disclaimer, the term of this patent is extended or adjusted under 35 U.S.C. 154(b) by 286 days.

(21) Appl. No.: 15/756,534

(22) PCT Filed: Sep. 1, 2016

(86) PCT No.: PCT/US2016/049974
§ 371 (c)(1),
(2) Date: Feb. 28, 2018

(87) PCT Pub. No.: WO2017/040836
PCT Pub. Date: Mar. 9, 2017

(65) Prior Publication Data
US 2018/0243710 A1  Aug. 30, 2018

Related U.S. Application Data

(60) Provisional application No. 62/213,968, filed on Sep. 3, 2015.

(51) Int. Cl.
| | | |
|---|---|---|
| *A61K 36/00* | (2006.01) | |
| *B01J 6/00* | (2006.01) | |
| *C07D 311/80* | (2006.01) | |
| *C07D 311/78* | (2006.01) | |
| *C07C 37/50* | (2006.01) | |
| *B01J 19/24* | (2006.01) | |
| *B01L 7/00* | (2006.01) | |
| *A61K 36/185* | (2006.01) | |
| *B01J 19/00* | (2006.01) | |
| *C07C 37/56* | (2006.01) | |

(52) U.S. Cl.
CPC ............ *B01J 6/008* (2013.01); *A61K 36/185* (2013.01); *B01J 19/0013* (2013.01); *B01J 19/24* (2013.01); *B01L 7/00* (2013.01); *C07C 37/50* (2013.01); *C07C 37/56* (2013.01); *C07D 311/78* (2013.01); *C07D 311/80* (2013.01); *B01J 2219/002* (2013.01); *B01J 2219/0006* (2013.01); *B01J 2219/00063* (2013.01); *B01J 2219/00135* (2013.01); *B01J 2219/00155* (2013.01); *B01J 2219/00204* (2013.01); *B01J 2219/00213* (2013.01); *B01J 2219/00225* (2013.01); *B01L 2200/147* (2013.01); *C07C 2601/16* (2017.05)

(58) Field of Classification Search
CPC ...................................................... A61K 36/00
USPC ............................................................ 424/725
See application file for complete search history.

(56) References Cited

PUBLICATIONS

I_Submit_This, "Cannabutter Recipe—95% Odorless Process", Jan. 19, 2012, Reddit, https://www.reddit.com/r/trees/comments/on7qp/cannabutter_recipe_95_odorless_process/.
Unknown Author, "Table 4 HPLC Data from Decarboxylation of THCA Herbal Material," Aug. 19, 2014, Imgur, https:imgur.com/p1r1mLx.
Glas-Col(R), "2006-2007 CE Product Catalog," Jan. 1, 2006, http://photos.labwrench.com/equipmentManuals/2839-1880.pdf.
Smuv, "Heating Mantle repair/construction," Mar. 21, 2011, The art and science of amateur experimentalism, http://www.sciencemadness.org/talk/viewthread.php?tid=15844.

*Primary Examiner* — Michael V Meller
(74) *Attorney, Agent, or Firm* — Fish & Richardson P.C.; Frank L. Gerratana

(57) ABSTRACT

A waterless decarboxylation device used to decarboxylate *cannabis* is described. For example, the device could include a product container to contain an amount of raw *cannabis* plant material, a heating container configured to surround and contact the product container, a heater in contact with the heating container, a foam layer surrounding the product container and heating container, at least one sensor configured to detect the temperature of the heating container, a lid that encloses the product container and fluidly seals it from the environment, and a controller configured to control power to the heater in response to signals sent from the at least one sensor indicating whether the heating container has reached a threshold temperature.

8 Claims, 9 Drawing Sheets

WATERLESS DECARBOXYLATION

RELATED APPLICATIONS

This application is a U.S. national stage application under 35 USC § 371 of International Application No. PCT/US2016/049974, filed on Sep. 1, 2016, which claims benefit of and priority to U.S. provisional applications 62/213,968, filed on Sep. 3, 2015, the entire contents of all applications which are incorporated herein by reference.

TECHNICAL FIELD

This invention relates to waterless decarboxylation of cannabis.

BACKGROUND

In its natural state, the tetrahydrocannabinol (THC) in cannabis is found as its biosynthesized precursor, tetrahydrocannabinolic acid (THCA). To activate this potential THC and other cannabinoids, a carboxyl group must be removed by heat. In practice, available THCA in cannabis is "decarboxylated" to THC by the heat of smoking or cooking. The THC may then be delivered relatively rapidly through the lungs when smoked or more slowly in the gastrointestinal tract when eaten. Preparations other than smoking may necessitate extraction of the active cannabinoids into a secondary medium. Smoking cannabis necessarily creates harmful carcinogens through destructive pyrolysis of numerous plant compounds, as well as irritation to the lung tissue. Eating cannabis tends to require a significant period of time (e.g., 30-60 minutes or more) before onset of effects, and the uptake through the gastrointestinal tract may be uneven and incomplete.

SUMMARY

A waterless decarboxylation device can be used to decarboxylate cannabis. For example, the device could include a product container to contain an amount of raw cannabis plant material, a heating container configured to surround and contact the product container, a heater in contact with the heating container, a foam layer surrounding the product container and heating container, at least one sensor configured to detect the temperature of the heating container, a lid that encloses the product container and fluidly seals it from the environment, and a controller configured to control power to the heater in response to signals sent from the at least one sensor indicating whether the heating container has reached a threshold temperature. In some aspects, the controller is configured to control power to the heater to maintain the heating container temperature at the detected threshold temperature for a period of time. The period of time is 30 to 90 minutes. The period of time is 60 minutes. The threshold temperature is 105° C. At least one second sensor is configured to detect the temperature at a second position within the waterless decarboxylation device at a distance from the heating container. The second position is at least one of the heating layer, the foam layer, the bottom of the heating layer contacting the product container, and a space inside a canister base attached to the canister. The controller is configured to control power to the heater to so that the temperature detected at the second position is not above a critical temperature. The wherein the critical temperature is 105-115° C. A canister base attached to the foam layer, the canister base comprising a button and/or a light.

The device could be used to decarboxylate an amount of raw cannabis plant material sufficient to deliver an effective dose of at least one pharmacologically active cannabinoid present in the decarboxylated cannabis plant material. For example, the device could be used by placing the amount of raw cannabis plant material into the device, sealing the device, and heating the device to about 103° C. to about 110° C. for a period of from about 30 minutes to about 90 minutes to decarboxylate the amount of raw cannabis plant material inside the waterless decarboxylation device. In some aspects, heating the device comprises heating the device so that it does not surpass a critical temperature. The wherein the critical temperature is 105-115° C. The method further comprises cooling the device to a safe temperature after the heating. Heating the device comprises pressing a button on the waterless decarboxylation device.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
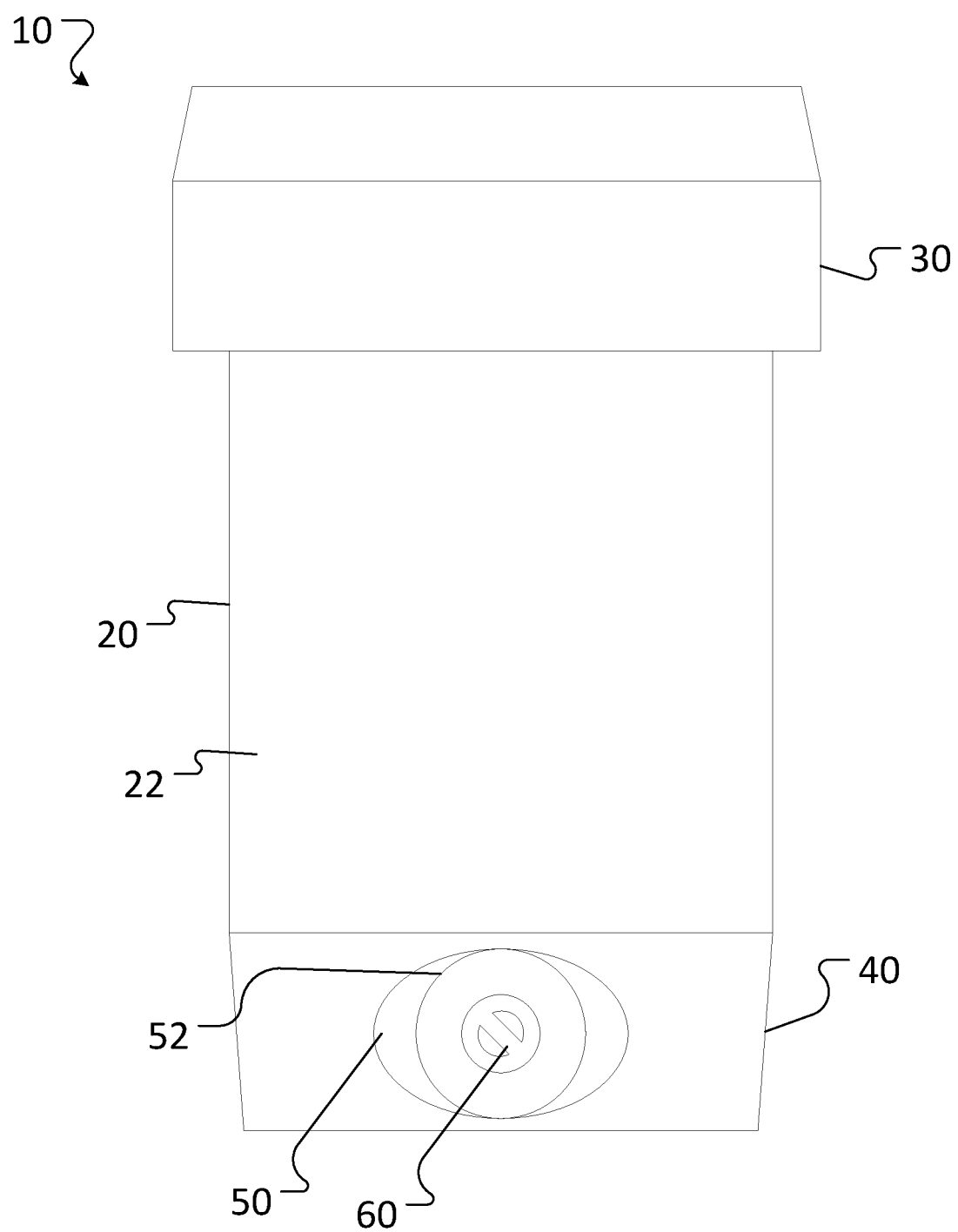
FIG. 1 is an external view of the waterless decarboxylation device.

The waterless decarboxylation device uses heat to remove a carboxyl group from, or decarboxylate, the tetrahydrocannabinolic acid in cannabis to produce THC. A user places cannabis into the waterless decarboxylation device, which then seals and heats the cannabis to the ideal decarboxylation temperature of 103° C.-110° C. The waterless decarboxylation device does not use boiling water or steam to heat the cannabis. Boiling water tends to reach a maximum temperature of 100° C., which is too low for the most efficient decarboxylation reaction. Further, water boils at different temperatures depending on altitude, which leads to imprecision in the decarboxylation process and varying outcomes using that method. The waterless decarboxylation device also evenly distributes the heat, which tends to increase the efficiency and uniformity of the decarboxylation reaction, and maintains this ideal decarboxylation temperature for a period of time, such as 60 minutes, to allow the reaction to reach completion.

The decarboxylated *cannabis* plant material has at least one pharmacologically active cannabinoid present as an active ingredient. The at least one pharmacologically active cannabinoid comprises tetrahydrocannabinol. The tetrahydrocannabinol is present in an amount from about 1% to about 40% total weight of the decarboxylated *cannabis* plant material. In some examples, the tetrahydrocannabinol is present in a dose range from about 2 mg to about 500 mg. The decarboxylated *cannabis* plant material contains at least 90% of the maximum amount of tetrahydrocannabinol that could theoretically be present as a result of decarboxylation of the maximum amount of THCA present in the *cannabis* plant material.

Decarboxylating the raw *cannabis* plant material activates at least one pharmacologically active cannabinoid present in the raw *cannabis* plant material. As used herein, "activates" refers to converting an inactive precursor into a pharmacologically active ingredient. Decarboxylating the raw *cannabis* plant material converts at least one inactive precursor acid present in the raw *cannabis* plant material into at least one pharmacologically active cannabinoid (e.g., conversion of THCA precursor to THC).

In contrast to conventional methods of preparing *cannabis* dosage forms which subsequently process decarboxylated *cannabis*, for example by extracting the pharmacologically active THC from the plant material itself, decarboxylating the raw *cannabis* plant material is the only processing step that is required to prepare an ingestible dosage in accordance with the present invention. That is, decarboxylating the raw *cannabis* plant material activates at least one pharmacologically active cannabinoid in the raw *cannabis* plant material so that the decarboxylated *cannabis* plant material is suitable for ingestible or topical administration in its plant form without subsequent processing of the decarboxylated *cannabis* plant material. In particular, decarboxylating the raw *cannabis* plant material as described herein activates at least one pharmacologically active cannabinoid present in the raw *cannabis* plant material so that the decarboxylated *cannabis* plant material can be ingested in the absence of subjecting the raw *cannabis* plant material or the decarboxylated *cannabis* plant material to a processing technique, such as admixing, condensation, decoction, distillation, expression, extraction selected from the group consisting of aqueous extraction, solvent extraction, ethanolic extraction, gas extraction, $CO_2$ extraction, extrusion, filtration, isolation, maceration, percolation, precipitation, pulverization, purification, solvent casting, spheronization, sublimation, volatilization, and winterization. The methods described herein prepare an ingestible dosage form comprising the decarboxylated *cannabis* plant material for immediate ingestion to administer at least one pharmacologically active cannabinoid present in the decarboxylated *cannabis* plant material without having to subject the decarboxylated *cannabis* plant material to further processing, such as admixing, condensation, decoction, distillation, expression, extraction selected from the group consisting of aqueous extraction, solvent extraction, ethanolic extraction, gas extraction, $CO_2$ extraction, extrusion, filtration, isolation, maceration, percolation, precipitation, pulverization, purification, solvent casting, spheronization, sublimation, volatilization, and winterization.

The methods of decarboxylating raw (i.e., pre-decarboxylated) *cannabis* plant material described result in the formation of decarboxylated *cannabis* plant material that contains at least 70% of the maximum amount of pharmacologically active cannabinoids (e.g., tetrahydrocannabinol and cannabidiol) that could theoretically be present as a result of decarboxylation of the maximum amount of their pharmacologically inactive precursor acids (e.g., THCA and cannabidiolic acid [CBDA]) present in the *cannabis* plant material (i.e., at least 70% of the pharmacologically inactive precursor acids present in the *cannabis* plant material are decarboxylated to their pharmacologically active cannabinoid form). Preferably, the methods of decarboxylating raw *cannabis* plant material herein result in the formation of decarboxylated *cannabis* plant material contains at least 71%, at least 72%, at least 73%, at least 74%, 75%, at least 76%, at least 77%, at least 78%, at least 79%, at least 80%, at least 81%, at least 82%, at least 83%, at least 84%, at least 85%, at least 86%, at least 87%, at least 88%, or at least 89% of the maximum amount of pharmacologically active cannabinoids that could theoretically be present as a result of decarboxylation of the maximum amount of their pharmacologically inactive precursor acids present in the *cannabis* plant material. More preferably, the methods of decarboxylating raw *cannabis* plant material result in the formation of decarboxylated *cannabis* plant material contains at least 90% of the maximum amount of pharmacologically active cannabinoids that could theoretically be present as a result of decarboxylation of the maximum amount of their pharmacologically inactive precursor acids present in the *cannabis* plant material. Even more preferably, the methods of decarboxylating raw *cannabis* plant material described herein result in the formation of decarboxylated *cannabis* plant material contains at least 91%, at least 92%, at least 93%, at least 94%, at least 95%, at least 96%, at least 97%, at least 98%, or at least 99% of the maximum amount of pharmacologically active cannabinoids that could theoretically be present as a result of decarboxylation of the maximum amount of their pharmacologically inactive precursor acids present in the *cannabis* plant material. The methods of decarboxylating raw *cannabis* plant material described herein result in the formation of decarboxylated *cannabis* plant material contains the maximum amount (i.e., 100% less any minor or negligible loss of product due to undesirable degradation [e.g., to cannabinol, oxidation/pyrolytic degradation]) of pharmacologically active cannabinoids that could theoretically be present as a result of decarboxylation of the maximum amount of their pharmacologically inactive precursor acids present in the *cannabis* plant material (i.e., at least 100% of the pharmacologically inactive precursor acids present in the *cannabis* plant material are decarboxylated to their pharmacologically active cannabinoid form regardless of minor or negligible loss of product due to undesirable reactions or unwanted degradation [e.g., degradation to cannabinol, oxidation/pyrolytic degradation]).

One way in which the maximum amount of THC that could theoretically be available assuming full decarboxylation under ideal conditions can be calculated using the formula: Max THC=THC+THCA*0.877. The same formula can be used to calculate the maximum CBD, e.g., by replacing THC and THCA with CBD and CBDA, respectively. For the avoidance of double, when calculating the maximum amount of THC that could theoretically be available using this formula the phrase "at least X %" of the maximum amount of pharmacologically active cannabinoids that could theoretically be present as a result of decarboxylation of the maximum amount of their pharmacologically inactive precursor acids present in the *cannabis* plant material" refers to at least X % of the Max THC value calculated using the formula. The methods of decarboxylating raw cannabis plant material described herein result in the formation of decarboxylated cannabis plant material that contains cannabinol in an amount less than 0.5%, less than 0.4%, less than 0.3%, less than 0.2%, less than 0.1 total weight of the decarboxylated cannabis plant material. Preferably, the methods described result in the formation of decarboxylated cannabis plant material that contains cannabinol in an amount below quantifiable limits with respect to the total weight of the decarboxylated cannabis plant material. Preferably, decarboxylation of the amount of raw cannabis plant material results in the simultaneous pasteurization of the decarboxylated cannabis plant material, for example, to inactivate live pathogens (e.g., *Aspergillus* fungus) which would render the cannabis unsuitable for human consumption. The methods, apparatuses, and systems of the present invention are well adapted to simultaneously carry out decarboxylation and pasteurization of raw cannabis so that the resulting decarboxylated cannabis plant material is immediately suitable for suitable for ingestion, without requiring a pre- or post-decarboxylation pasteurization step, for example using an autoclave.

Decarboxylating the amount of raw cannabis plant material comprises heating an amount of raw cannabis plant material at a temperature of from about 103° C. to about 110° C. for a period of from about 30 minutes to about 90 minutes, thereby decarboxylating the amount of raw cannabis plant material.

In some embodiments, decarboxylating the amount of raw cannabis plant material comprises heating the amount of raw cannabis plant material in an device at a temperature of from about 105° C. to about 110° C. for a period of from about 20 to 60 minutes which results in the formation of decarboxylated cannabis plant material that contains at least 90% of the maximum amount of THC and/or at least 80% of the maximum amount of CBD that could theoretically present as a result of decarboxylation of the maximum amount of both THCA and/or CBDA, respectively, present in the amount of raw cannabis plant material. In contrast, an apparatus for decarboxylation using boiling water as a heat source for about 60 minutes (e.g., described in U.S. Pat. No. 4,279,824) only achieves a decarboxylation completeness for THC of 64%, and does not exceed a decarboxylation completeness of 67% for CBD even after 4 hours of decarboxylation using that apparatus.

The at least one pharmacologically active cannabinoid is cannabidiol and the at least one pharmacologically active cannabinoid's inactive precursor is cannabidiolic acid. The cannabidiolic acid is present prior to decarboxylation in an amount from about 1% to about 40% total weight of the raw cannabis plant material. The cannabidiol is present after decarboxylation in an amount from about 1% to about 40% total weight of the decarboxylated cannabis plant material. The temperature range is from about 85° to about 125° and the period of time is between 60 minutes and 120 minutes. The decarboxylated cannabis plant material contains at least 80% of the maximum amount of cannabidiol that could theoretically be present as a result of decarboxylation of the maximum amount of cannabidiolic acid present in the raw cannabis plant material. The temperature range is 103° C. to 115° C. and the period of time is between 20 minutes and 120 minutes. In some embodiments, the decarboxylated cannabis plant material contains at least 90% of the maximum amount of cannabidiol that could theoretically be present as a result of decarboxylation of the maximum amount of cannabidiolic acid present in the raw cannabis plant material. This can be achieved with a temperature range from about 103° to about 115° and the period of time is between about 60 to 120 minutes.

The waterless decarboxylation device can include a device that may contain an initial amount of oxygen present consisting of atmospheric oxygen that enters the device when the amount of raw cannabis plant material enters the device. The initial amount of oxygen present in the device is generally not enough to cause significant oxidative degradation of the decarboxylated cannabis plant material. The device prevents atmospheric oxygen from entering the device during decarboxylation of the cannabis plant material, thereby minimizing oxidative degradation of the decarboxylated cannabis plant material. The device displaces an amount of fluid (e.g., air) that entered the device upon placing the amount of raw cannabis plant material in the device to reduce the oxygen content in the device, without permitting additional atmospheric oxygen to enter the device.

Decarboxylating the amount of raw cannabis plant material comprises: (i) placing the amount of raw cannabis plant material into the waterless decarboxylation device (ii) sealing the device, wherein sealing limits the oxygen content in the device to an initial amount of atmospheric oxygen present in air that enters the device during step (i) prior to sealing the device; and (iii) heating the device indirectly with a heat source outside the device at a temperature of from about 103° C. to about 115° C. for a period of from about 60 minutes to about 120 minutes to decarboxylate the amount of raw cannabis plant material inside waterless decarboxylation device.

FIG. 1 shows an exterior view of the waterless decarboxylation device 10. The waterless decarboxylation device 10 includes a canister body 20 which fits with a lid 30. The canister body 20 is generally cylindrical, and includes a canister shell 22 which is hard and protects the inner contents of the canister body 20. The canister body 20 is joined with a canister base 40. During use, the canister base 40 sits on a flat surface such as a table or counter. The canister base 40 shown in FIG. 1 is tapered, however the canister base can be cylindrical as well. A user display interface 50 is also positioned on an exterior surface of the canister base 40. The user display interface 50 includes a button 52 that the user can press to begin the heating and cooling procedure of the waterless decarboxylation device 10. The user display interface also includes a light 60 that indicates the status of the waterless decarboxylation device 10 to the user. The light 60 can be turned on or off, and when on can show one or more colors, for example, red and green. The light 60 and the button 52 are shown as coincident or overlapping in FIG. 1, however the light 60 and button 52 may be combined into a single item, or alternatively may be located side by side.

Figure 2:
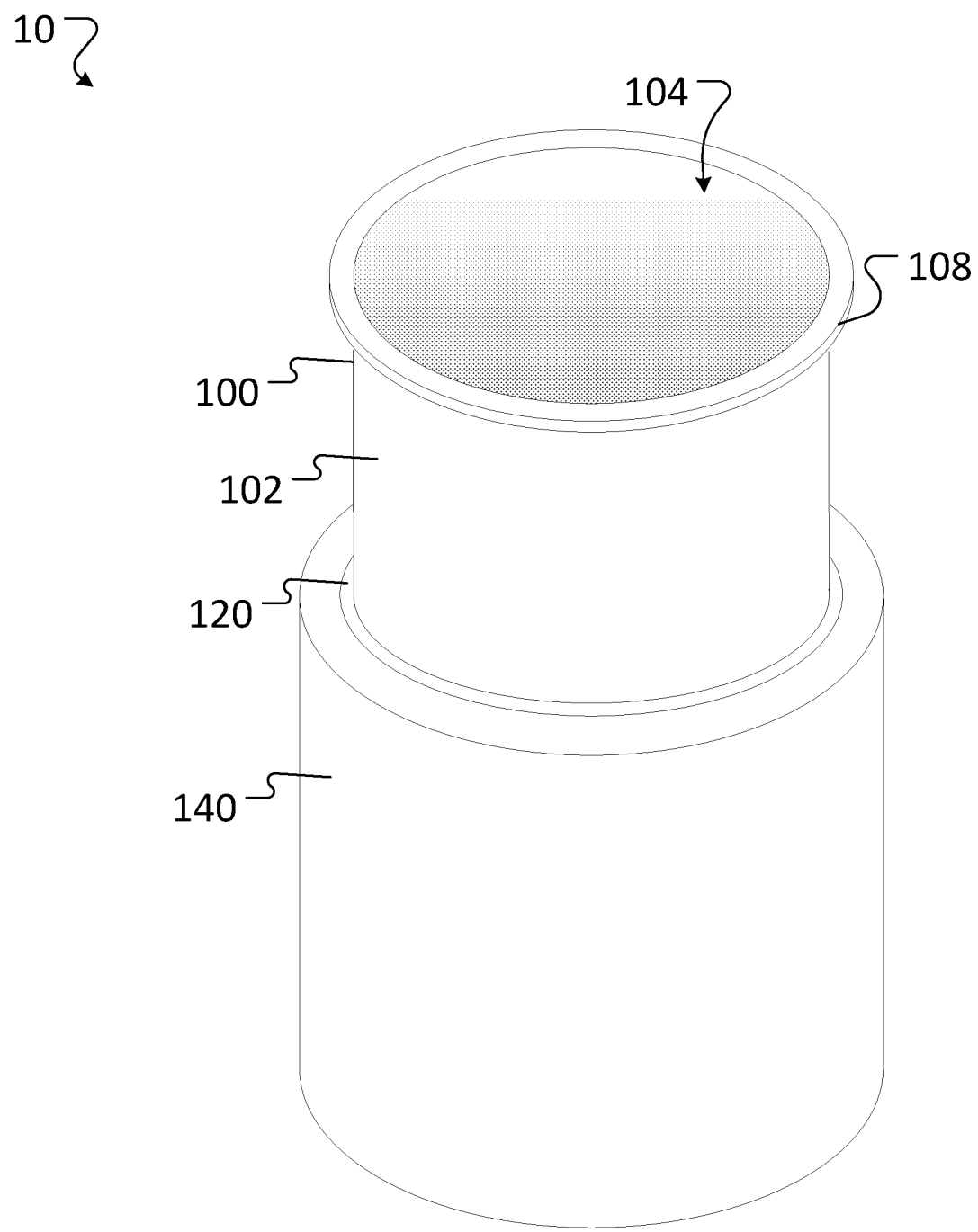
FIG. 2 is a perspective partially disassembled view showing portions of the inside of the waterless decarboxylation device with the inner canister raised.
Figure 3:
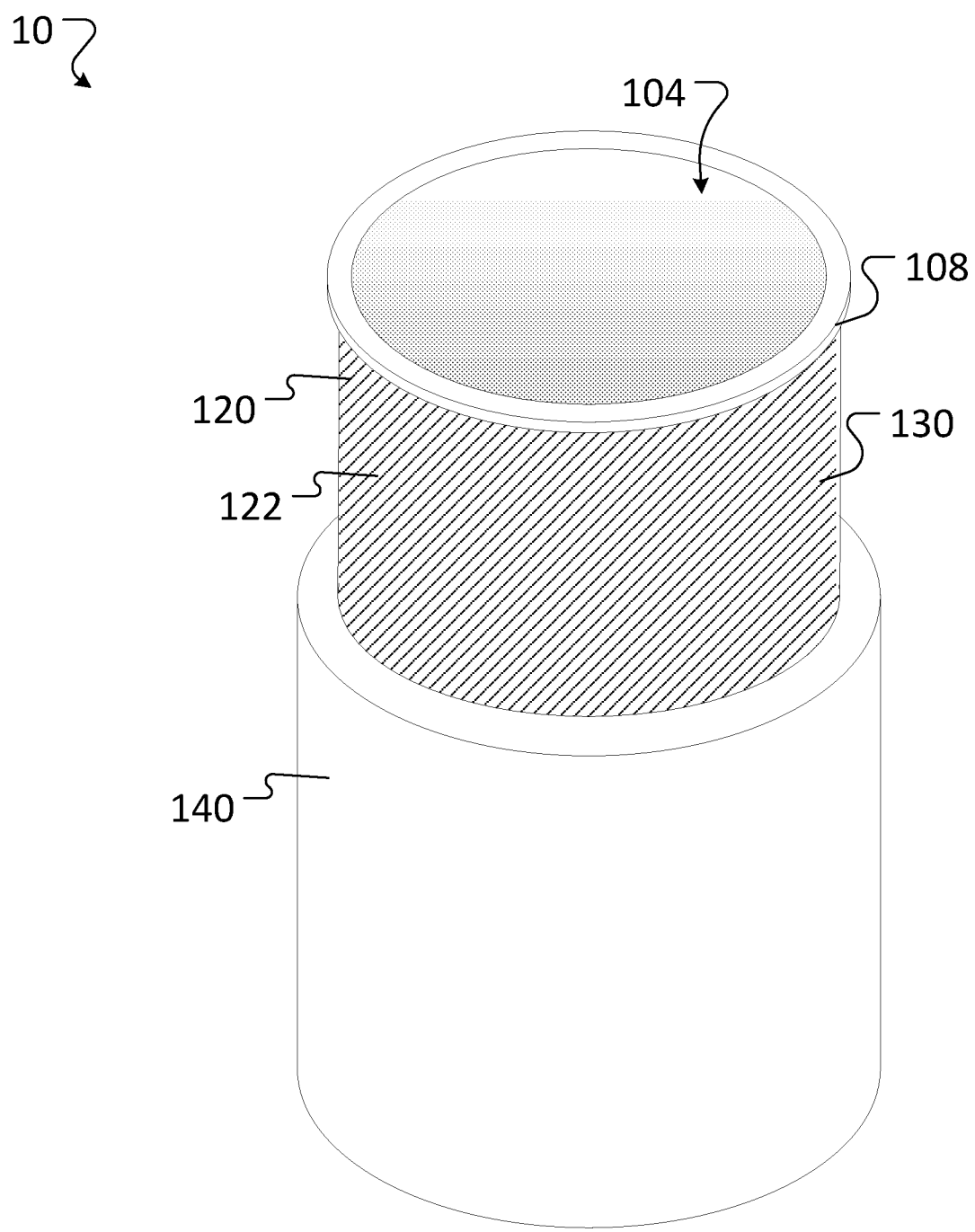
FIG. 3 is a perspective partially disassembled view showing portions of the inside of the waterless decarboxylation device with the heating cylinder raised.
Figure 4:
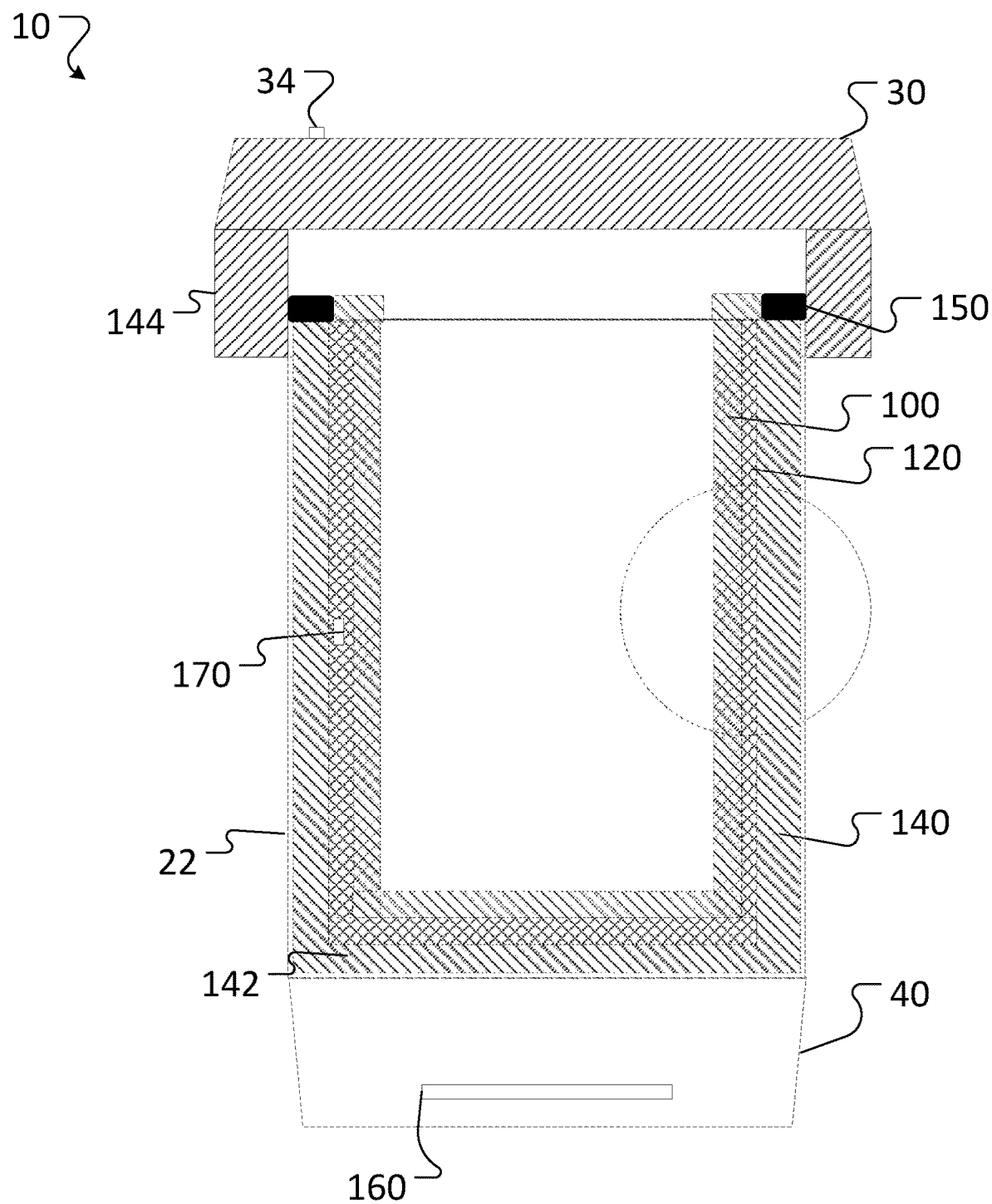
FIG. 4 is a cross section of an embodiment of the waterless decarboxylation device.

FIG. 2 shows the inside of canister body 20 with the canister shell 22 removed. Canister body 20 is shown to include a series of cylinders that fit one inside the other, and which all fit within the canister shell 22. The innermost cylinder is a receptacle or product container 100 that holds the cannabis to be decarboxylated. This product container 100 can slide up and down, that is, vertically, and in FIG. 2 is shown in a raised position relative to the other components. The product container 100 is generally cylindrical with a smooth outer surface 102, and inner surface 104 which contacts the cannabis. As best seen in FIG. 4, the product container 100 has a bottom portion that is flat and supports the cannabis. The product container 100 also has a circumferential lip 108 at its upper surface so that the user can easily grasp the container and move it up and down. The product container 100 is slidable in and up/down direct for ease of use, allowing the user to raise the container or remove it from the rest of the canister body 20 in order to easily place the *cannabis* inside of the product container 100. Once the *cannabis* is placed inside the user then pushes the product container 100 back down inside the remainder of the canister body 20 so that it is nestled inside the other cylinders.

Referring to FIGS. 2-4B, the next layer circumferentially external to the product container 100 is the heating layer 120. Like the product container 100, the heating layer 120 is generally cylindrical with an outer surface 122 and an inner surface 124, and a flat bottom portion that connects the cylindrical walls. Once the product container 100 is in place, the product container 100 is surrounded by the heating cylinder 120.

Figure 4A:
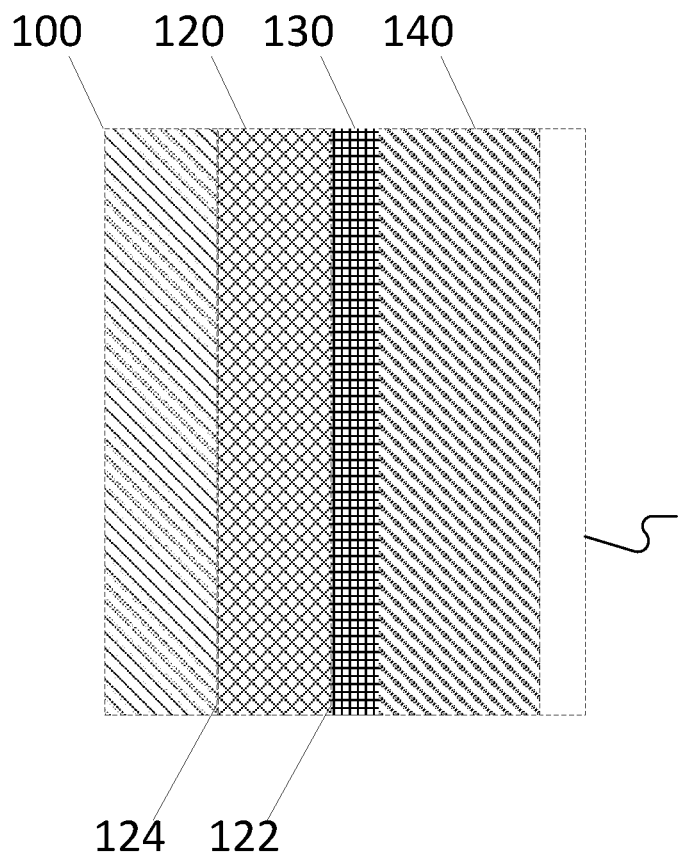
FIGS. 4A and 4B are enlargements of the area indicated in FIG. 4, showing two embodiments of the placement of the heater in the waterless decarboxylation device.
Figure 4B:
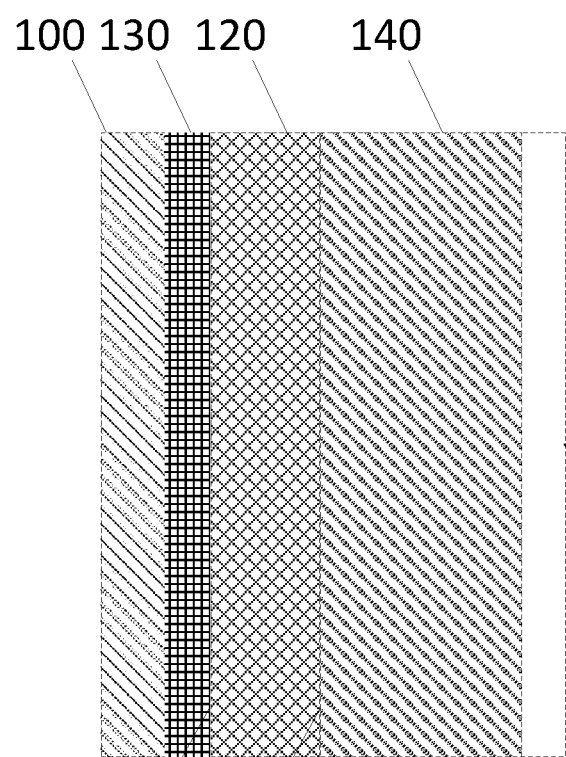

As shown in FIGS. 2 and 4A, the heating cylinder 120 has a flexible heating sheet 130 applied on the outer surface 122 of the heating cylinder 120. Alternatively, as shown in FIG. 4B, the heating sheet 130 can be located on the inner surface 124 of the heating cylinder 120. The heating sheet 130 is also known as a thermal blanket, and comprises a thin, flexible silicone wafer that can be wrapped around the heating cylinder 120. Such thermal blankets are known in the art, for example those produced by Birk Manufacturing. The heating sheet 130 is adhesive and can be adhered to the inner surface 124 or outer surface 122 of the heating cylinder 120. The heating sheet 130 can also be applied to the bottom portion of the heating cylinder 120.

When the heating sheet 130 is activated, the heat is transferred to the heating cylinder 120 and via conduction to the product container 100 and then via conduction and radiation to the *cannabis* inside the product container 100.

Outside the heating cylinder 120 is a foam layer 140 to thermally isolate the product inside the waterless decarboxylation device 10 from the environment and its ambient heating conditions and to evenly distribute the heat. The foam layer 140 surrounds and contacts the heating layer 120 on the inner surface of the foam layer 140 (outer surface 122 of the heating layer 120) and the canister shell 22 on the outer surface of the foam layer 140 (inner surface of the canister shell 22), and maximizes the heat transfer from the heating element to the *cannabis* within the product container 100. As shown in FIG. 4, the foam protection can extend onto the bottom of the canister shell 22 with bottom protection foam layer 142. Foam may also extend around the surface of canister base 40. Foam layer 140 may can be composed of foam, or any other thermally isolating material suitable from preventing or reducing thermal transmission from the inside of the waterless decarboxylation device 10 to the environment.

Still referring to FIG. 4, on top of all the cylinders is a lid 30. The lid 30 can also have a foam layer 144 within the lid's outer shell to ensure even heating and to prevent heat loss from the product container 100 to the environment. The lid 30 can have a valve or steam hole 34 to allow heated air to escape the inside of the waterless decarboxylation device 10. The lid 30 is shown in snap-fittable engagement with the canister body 20 around the circumferential rim of canister body 20. Although the mechanism of releasably engaging lid 30 and canister body 20 is shown, alternate engagement mechanisms may be employed, such as regularly spaced projections radiating inwardly from the inner surface of lid 30 to mate with corresponding detents disposed in the outer upper surface of canister body 20, or a threaded connection between an inner surface of the lid 30 and an upper portion of the canister body 20. Other engagement mechanisms could be used.

Figure 5:
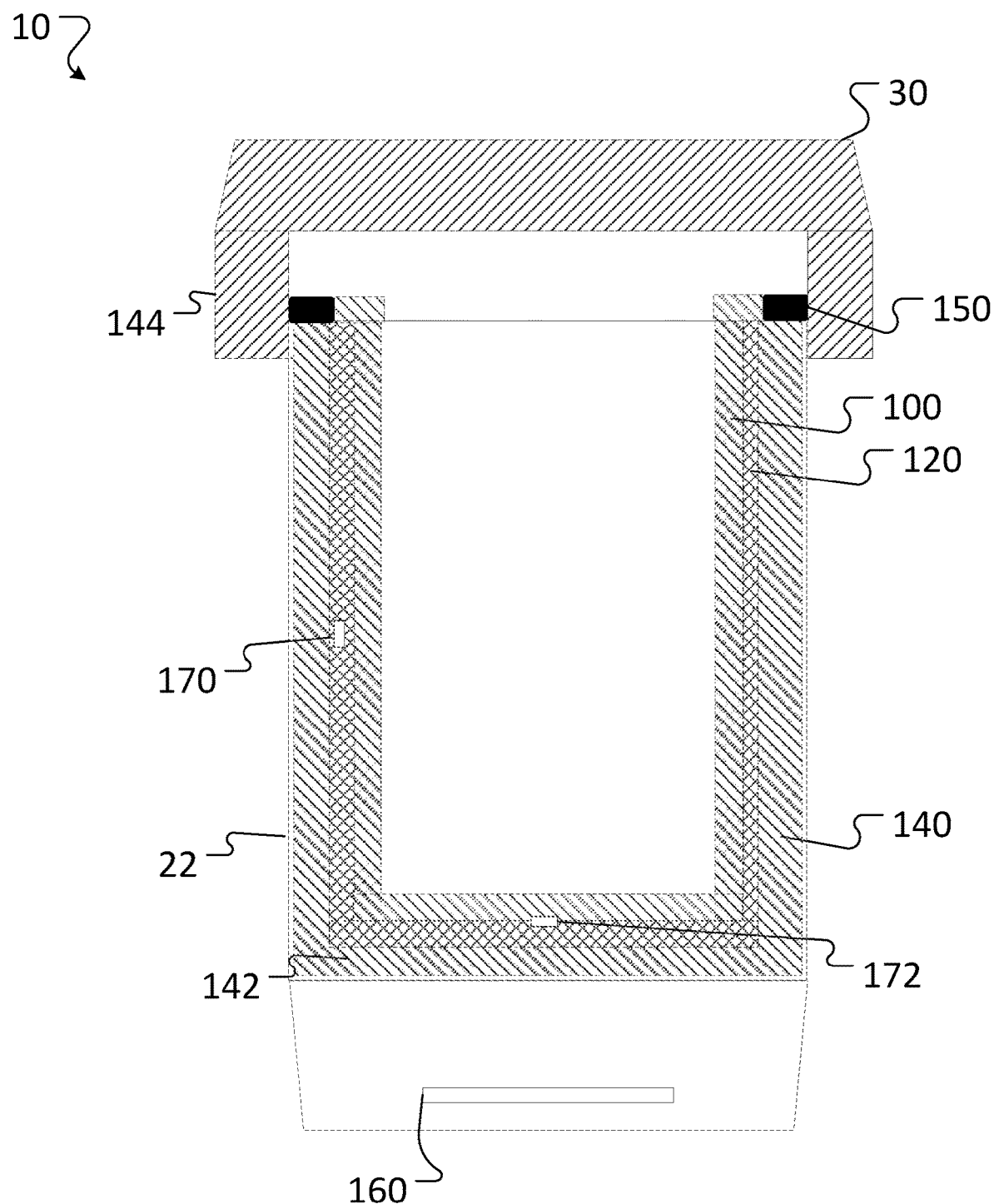
FIG. 5 is a cross section of a second embodiment of the waterless decarboxylation device.

The lid 30 is made to be airtight to prevent oxygen from entering the product container 100 during the heating process. For example, the lid 30 can be preferentially constructed out of silicone. Referring to FIGS. 4 and 5, the waterless decarboxylation device 10 can include an additional sealing element to reduce the amount of oxygen that leaks from the environment to the inside of the waterless decarboxylation device 10 by fluidly disconnecting the inside of the waterless decarboxylation device 10 from the environment. For example, seal 150 can be located between the lid 30 and the canister body 20. The seal 150 can be attached to an inner surface of the lid 30, the upper surface of the foam layer 140, or the top of the product container 100. The seal 150 can be O-ring.

The product container 100 and heating cylinder 120 can be constructed of a variety of suitable materials that efficiently conduct heat, such as various metals. The canister body 20 and lid 30 can be constructed of a variety of materials which are suitable, including, but not limited to, plastic, glass, silicone, food-grade butyl rubber, latex, aliphatic polyesters, natural rubber, metal, metal foils, polytetrafluoroethylene, biopolymers such as liquid wood, modified casein, polyhydroxyalkanoate polyesters, including polyhydroxybutrate, polyhydroxyvalerate, polylactic acid, starch based polyesters, keratin processed with methyl acrylate, hemp polymers, hemp plastic, hemp composite polymers, and combinations thereof. The canister body 20 is preferably constructed of a cylindrical shape, as shown in FIG. 1. The various cylindrical layers can be modified to taper inwardly as wall portions extend toward the canister base 40 so that an amount of raw *cannabis* plant material to be decarboxylated can aggregate together in the product container 100, for example, to ensure consistent heating of the amount of the raw *cannabis* plant material.

Referring again to FIGS. 4 and 5, the canister base 40 contains an empty space that houses a circuit board 160 with a microprocessor or microcontroller that controls the heating of the heating sheet 130. The canister base 40 that contains the circuit board 160 is located below and attached to the canister shell 22 with a screw or other fastening mechanism.

The circuit board 160 also monitors one or more sensors in the waterless decarboxylation device 10. For example, as shown in FIG. 4, there is at least one first sensor 170 located on the heating layer 120. The first sensor 170, for example a thermocouple, detects the temperature of the heating layer 120 and sends the signal to the circuit board 160. The first sensor 170 is preferably in contact with the heating sheet 130. Since the heating layer 120 is the hottest part of the waterless decarboxylation device 10, the first sensor 170 is reading the maximum temperature within the waterless decarboxylation device 10, and ensures that the temperature does not increase beyond a threshold temperature that may damage the *cannabis* or the decarboxylation process, e.g., beyond 105 to 115 C.

FIG. 5 shows an embodiment in which there are at least two positions for sensors in the waterless decarboxylation device 10. In addition to the at least one sensor 170 on the heating layer 120 there is a second sensor 172 within the waterless decarboxylation device 10 located at a distance from the at least one sensor 170. This second sensor 172 can be located within the internal space in canister base 40. Alternatively, the second sensor 172 can be embedded within the heating layer 120, the foam layer 140, or on the bottom of the heating layer 120 either contacting the product container 100, or open to the space within the canister base 40. The second sensor 172 may include sensors in one or more of these locations.

With the at least two sensors 170, 172 detecting the temperature at different locations, the second sensor 172 ensures that the temperature everywhere inside the canister shell 22 or the waterless decarboxylation device reaches the desired temperature (e.g., 105° C.). The first sensor 170 on the heating sheet 130 then works as a failsafe, measuring the hottest portion of the waterless decarboxylation device 10 so that the circuit board 160 ensures that the temperature is not above a threshold critical temperature (e.g., 105-115° C.).

Figure 6:
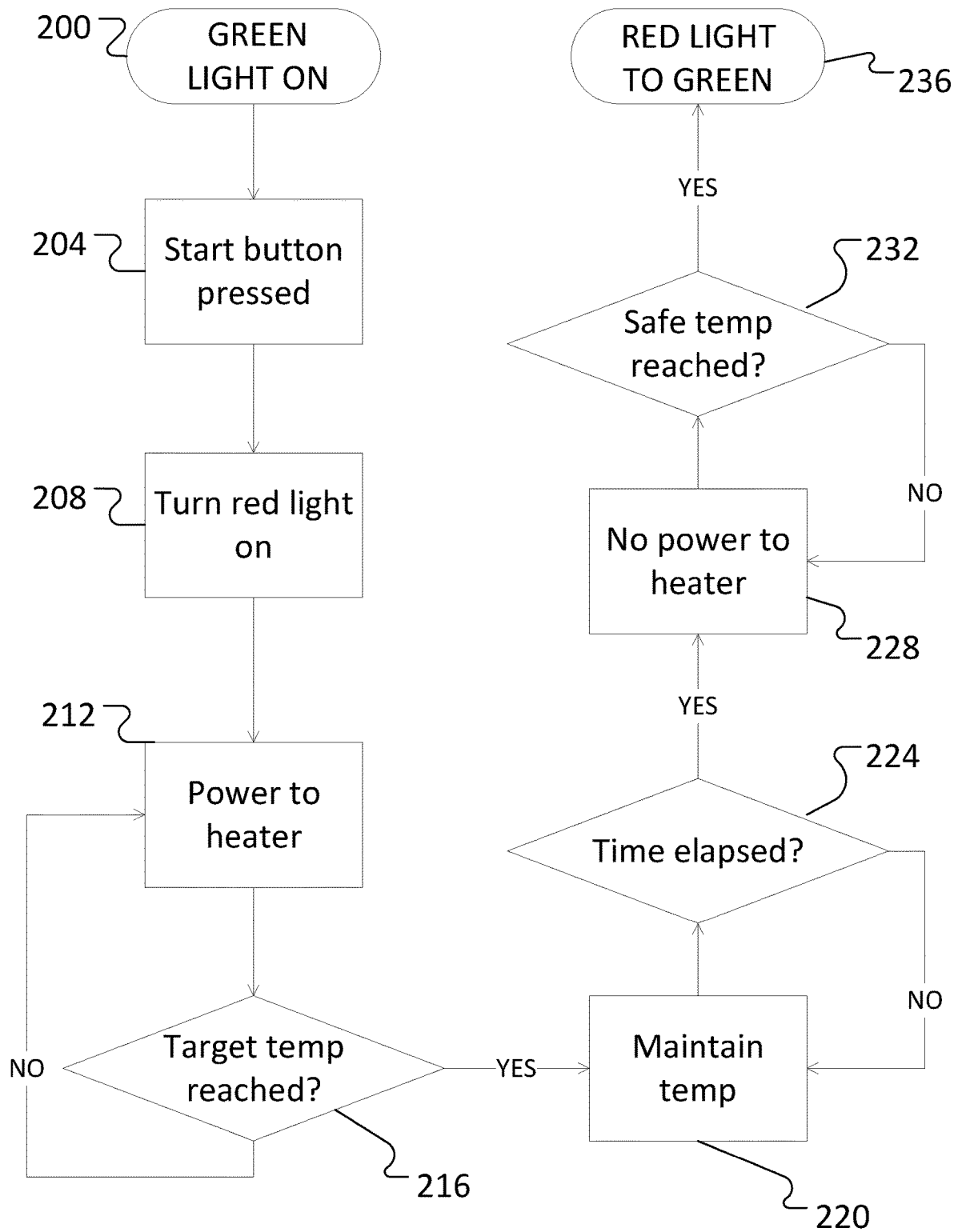
FIG. 6 is a flow chart of the heating algorithm of the device of FIG. 3.

FIG. 6 shows a flowchart describing the heating algorithm of the waterless decarboxylation device 10 with at least one first sensor 170 affixed to the heating sheet 130. The user first prepares the waterless decarboxylation device 10 for use by placing the *cannabis* inside the product container 100, and lowering the product container 100 into its active position (e.g., the position shown in FIG. 4) and then attaching the lid 30 to the canister body 20.

With the waterless decarboxylation device 10 connected to a power source (e.g., plugged in) the waterless decarboxylation device 10 is now ready to begin its heating cycle. At the start 200 of the cycle, the light 60 on the user display interface 50 shows green, indicating that power is flowing to the waterless decarboxylation device 10 but that the heat cycle has not begun and is ready for use. The user presses the button 52 on the user display interface 50. The waterless decarboxylation device 10 detects that the button 52 was pressed (step 204), and turn the light 60 from green to red, indicating to the user that the cycle has begun (step 208). At step 212, power begins flowing to the heater in heating sheet 130.

At step 216, the first sensor 170 detects the temperature. If the target temperature (e.g., the desired temperature or threshold maximum temperature) is not reached, then power continues to flow to the heating sheet 130, step 212. If the target temperature has been reached, the waterless decarboxylation device 10 then maintains the temperature by reducing or stopping power to the heating sheet 130 (step 220). When the first sensor 170 registers the target temperature, the waterless decarboxylation device 10 notes the time, and then continually checks if the desired heating time has elapsed (step 224). If not, the device returns to step 220 of maintaining the temperature until the elapsed time at the desired heat is reached (e.g., 105° C. for 60 minutes). When the elapsed time is detected, power is cut from the heater (step 228), and the first sensor 170 continues to monitor the internal temperature. If the temperature is above a safe level (step 232), the waterless decarboxylation device 10 continues to block incoming power until the system has cooled to the desired temperature, e.g., a safe temperature such as room temperature or near room temperature. At step 236 the light 60 which is showing red returns to green, indicating to the user that the cycle is complete.

Figure 7:
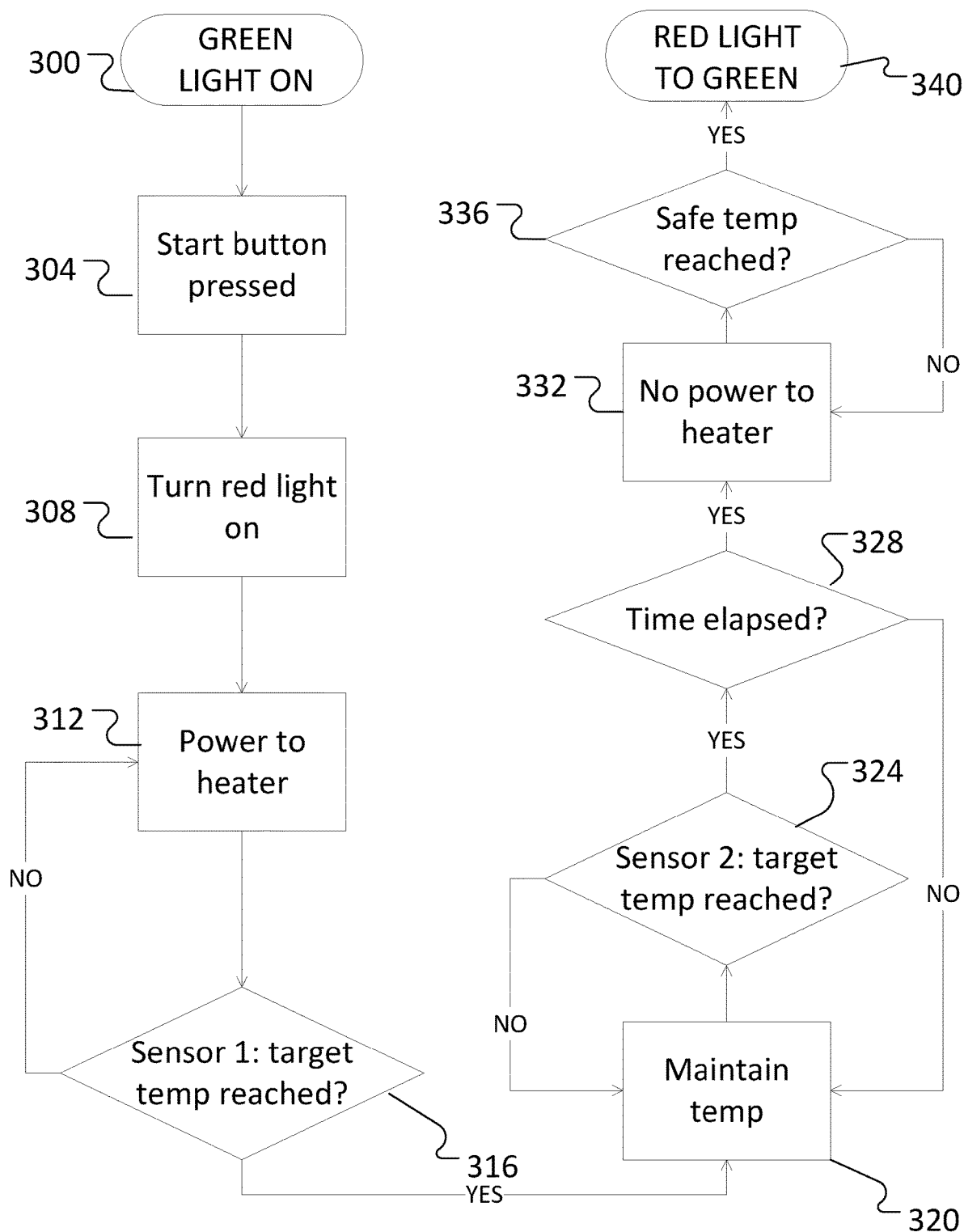
FIG. 7 is a flow chart of the heating algorithm of the device of FIG. 4.

FIG. 7 shows a flowchart describing the heating algorithm of the waterless decarboxylation device 10 with at least one first sensor 170 affixed to the heating sheet 130 and at least one second sensor 172 affixed elsewhere inside the canister shell 22 or inside the canister base 40. As for the previous embodiment, the user first prepares the waterless decarboxylation device 10 for use by placing the *cannabis* inside the product container 100, and lowering the product container 100 into its active position (e.g., the position shown in FIG. 5) and then attaching the lid 30 to the canister body 20.

With the waterless decarboxylation device 10 connected to a power source (e.g., plugged in) the waterless decarboxylation device 10 is now ready to begin its heating cycle. At the start 300 of the cycle, the light 60 on the user display interface 50 shows green, indicating that power is flowing to the waterless decarboxylation device 10 but that the heat cycle has not begun and is ready for use. The user presses the button 52 on the user display interface 50. The waterless decarboxylation device 10 detects that the button 52 was pressed (step 304), and turn the light 60 from green to red, indicating to the user that the cycle has begun (step 308). At step 312, power begins flowing to the heater in heating sheet 130.

At step 316, the first sensor 170 detects the temperature. If the target temperature (e.g., the desired temperature or threshold maximum temperature) is not reached, then power continues to flow to the heating sheet 130, step 312. If the target temperature has been reached, the waterless decarboxylation device 10 then maintains the temperature by reducing (or stopping) power to the heating sheet 130 (step 320).

At step 324, the second sensor 172 detects the temperature at its second location. If the target temperature (e.g., the desired temperature or threshold maximum temperature) is not reached at the second location, then power continues to flow to the heating sheet 130 to maintain the temperature sensed by first sensor 170, step 320. The waterless decarboxylation device 10 continues at this power level, while heat continues to flow and heat up the location of second sensor 172, indicating that the whole interior of the waterless decarboxylation device 10 has reached the target temperature.

When the second sensor 172 registers the target temperature, the waterless decarboxylation device 10 notes the time, and then continually checks if the desired heating time has elapsed (step 328). If not, the device returns to step 320 of maintaining the temperature until the elapsed time at the desired heat is reached (e.g., 105° C. for 60 minutes). When the elapsed time is detected, power is cut from the heater (step 332), and the first sensor 170 and/or the second sensor 172 continues to monitor the internal temperature. If the temperature is above a safe level (step 336), the waterless decarboxylation device 10 continues to block incoming power until the system has cooled to the desired temperature, e.g., a safe temperature such as room temperature or near room temperature. At step 340 the light 60 which is showing red returns to green, indicating to the user that the cycle is complete.

Although a light is described in the examples described above, any other suitable user interface element could be used to communicate the same information to the user. As another example, the device 10 could have a communication interface for communicating with an external device (e.g., a Bluetooth interface), and could send a notification to the external device (e.g., a smartphone, smartwatch, or other suitable device) which could then display information related to the notification on its user interface.

Figure 8:
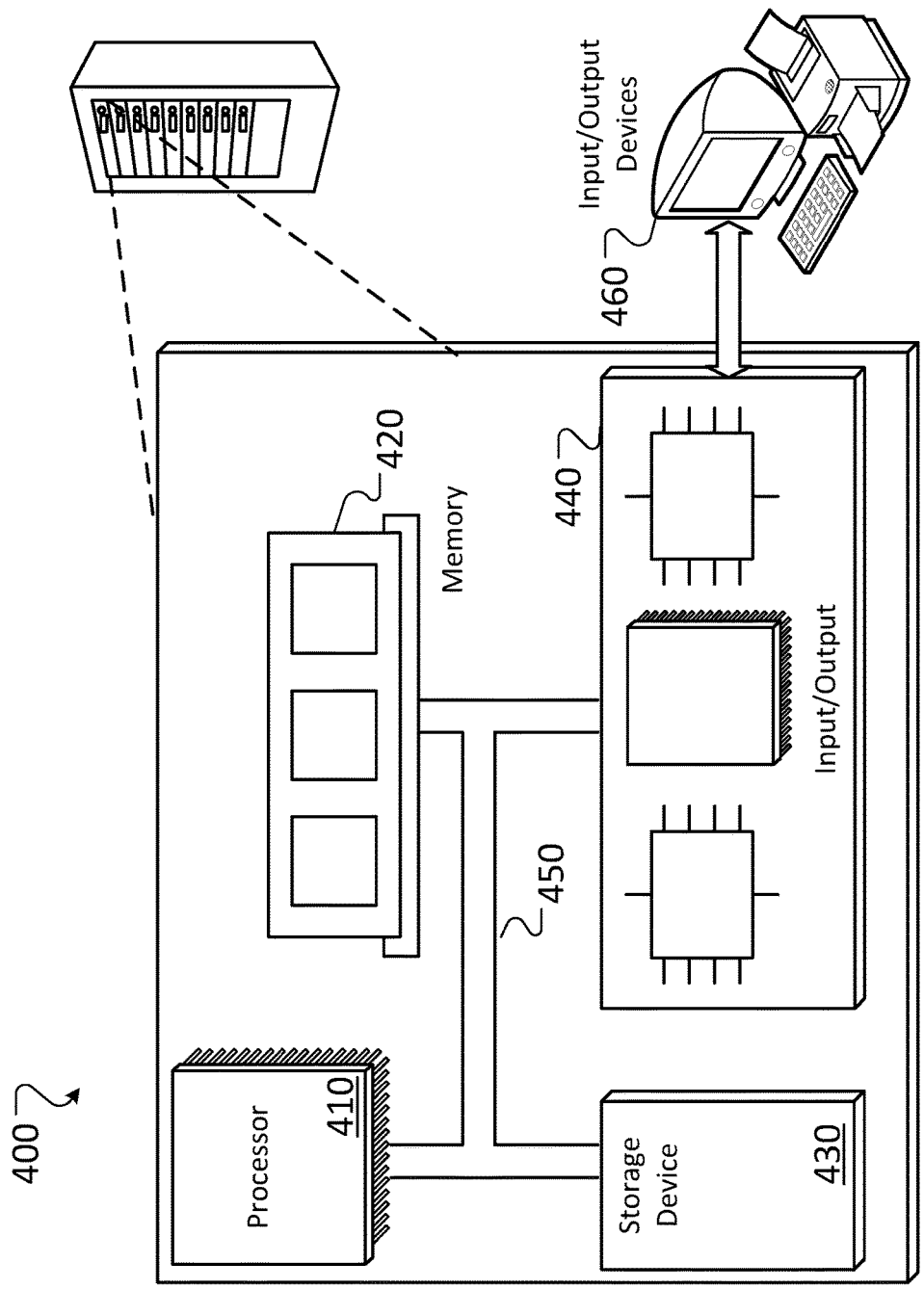
FIG. 8 is an example computer block diagram for controlling the waterless decarboxylation device.

FIG. 8 is a block diagram of an example computer system 400. For example, referring to FIG. 4 or 5, circuit board 160 could be a part of an example of the system 400 described here. The system 400 includes a processor 410, a memory 420, a storage device 430, and one or more input/output interface devices 440. Each of the components 410, 420, 430, and 440 can be interconnected, for example, using a system bus 450.

The processor 410 is capable of processing instructions for execution within the system 400. The term "execution" as used here refers to a technique in which program code causes a processor to carry out one or more processor instructions. The processor 410 is capable of processing instructions stored in the memory 420 or on the storage device 430. The processor 410 may execute operations such as waterless decarboxylation of *cannabis*.

The memory 420 stores information within the system 400. In some implementations, the memory 420 is a computer-readable medium. In some implementations, the memory 420 is a volatile memory unit. In some implementations, the memory 420 is a non-volatile memory unit.

The storage device 430 is capable of providing mass storage for the system 400. In some implementations, the storage device 430 is a non-transitory computer-readable medium. In various different implementations, the storage device 430 can include, for example, a hard disk device, an optical disk device, a solid-state drive, a flash drive, magnetic tape, or some other large capacity storage device. In some implementations, the storage device 430 may be a cloud storage device, e.g., a logical storage device including one or more physical storage devices distributed on a network and accessed using a network. In some examples, the storage device may store long-term data, such as the number of times the waterless decarboxylation device 10 has completed a cycle, the maximum and/or minimum temperatures recorded during each cycle, and/or the temperature profiles of each cycle. The input/output interface devices 440 provide input/output operations for the system 400. In some implementations, the input/output interface devices 440 can include one or more of a network interface devices, e.g., an Ethernet interface, a serial communication device, e.g., an RS-232 interface, and/or a wireless interface device, e.g., an 802.11 interface, a 3G wireless modem, a 4G wireless modem, etc. A network interface device allows the system 400 to communicate, for example, transmit and receive such data. In some implementations, the input/output device can include driver devices configured to receive input data and send output data to other input/output devices, e.g., keyboard, printer and display devices 460. In some implementations, mobile computing devices, mobile communication devices, and other devices can be used.

Referring to FIGS. 6 and 7, the described algorithms can be realized by instructions that upon execution cause one or more processing devices to carry out the processes and functions described above, for example, waterless decarboxylation of *cannabis*. Such instructions can include, for example, interpreted instructions such as script instructions, or executable code, or other instructions stored in a computer readable medium.

A server or database system can be distributively implemented over a network, such as a server farm, or a set of widely distributed servers or can be implemented in a single virtual device that includes multiple distributed devices that operate in coordination with one another. For example, one of the devices can control the other devices, or the devices may operate under a set of coordinated rules or protocols, or the devices may be coordinated in another fashion. The coordinated operation of the multiple distributed devices presents the appearance of operating as a single device.

In some examples, the system 400 is contained within a single integrated circuit package. A system 400 of this kind, in which both a processor 410 and one or more other components are contained within a single integrated circuit package and/or fabricated as a single integrated circuit, is sometimes called a microcontroller. In some implementations, the integrated circuit package includes pins that correspond to input/output ports, e.g., that can be used to communicate signals to and from one or more of the input/output interface devices 440.

Although an example processing system has been described in FIG. 7, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as storing, maintaining, and displaying artifacts can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, or a combination of one or more of them.

The term "system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM, DVD-ROM, and Blu-Ray disks. The processor and the memory can be supplemented by, or incorporated in, special purpose logic circuitry. Sometimes a server is a general purpose computer, and sometimes it is a custom-tailored special purpose electronic device, and sometimes it is a combination of these things. Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

A number of embodiments of the invention have been described. Nevertheless, it will be understood that various modifications may be made without departing from the spirit and scope of the invention. For example, in an embodiment, the method includes infusing the decarboxylated *cannabis* plant material with a flavorant, such as a flavorant described herein. Infusing the decarboxylated *cannabis* with a flavorant can be achieved in a variety of ways, for example, by contacting the decarboxylated *cannabis* plant material with an amount of flavorant and for a period of time sufficient to infuse the decarboxylated *cannabis* plant material with the flavoring. Preferably, the decarboxylated *cannabis* plant material is infused with a flavorant in a way that minimizes oxidative degradation of pharmacologically active cannabinoids in the *cannabis*. In an embodiment, the decarboxylated *cannabis* plant material is infused with flavorant prior to decarboxylating the *cannabis* plant material. For example, an amount of raw *cannabis* plant material can be contacted with flavorant in an inert, device for a period of time sufficient for the raw *cannabis* plant material to be infused with the flavorant, and the raw *cannabis* plant material infused with flavorant can be decarboxylated in accordance with the methods described herein. In an embodiment, the decarboxylated *cannabis* plant material is infused with flavorant during decarboxylation of the raw *cannabis* plant material. For example, an amount of raw *cannabis* plant material can be placed into a device along with the flavorant, and decarboxylation of the raw *cannabis* plant material can be carried out so that the resulting decarboxylated *cannabis* plant material is infused with the flavorant. In an embodiment, the decarboxylated *cannabis* plant material can be infused with flavorant after decarboxylating the raw *cannabis* plant material. For example, decarboxylated *cannabis* plant material can be placed into a storage medium (e.g., an inert storage medium) in contact with the flavorant until the decarboxylated *cannabis* plant material is infused with the flavorant.

Although the figures and description above refer to a cylindrical or near-cylindrical waterless decarboxylation device 10, the waterless decarboxylation device can be other shapes. For example, the waterless decarboxylation device can be spherical.

Accordingly, other embodiments are within the scope of the following claims.

What is claimed is:

1. A waterless decarboxylation device, comprising:
a) a sealed container;
b) a heating element which surrounds the sealed container and is configured to heat the sealed container to over 100° C. for over 30 minutes;
c) a foam layer surrounding the sealed container and the heating element;
e) at least one sensor configured to detect the temperature of the heating element;
f) a lid that encloses the container and fluidly seals it from the environment outside of the container; and
g) a circuit board comprising a controller configured to control power to the heating element in response to signals sent from the at least one sensor indicating whether the heating element has exceeded the temperature 100° C., wherein the controller is configured to control power to the heating element to maintain a temperature of the sealed container at 105° C. for 30 to 90 minutes, and wherein the controller is configured to control power to the heating element to so that the temperature detected at the heating element is not above 130° C.

2. The waterless decarboxylation device of claim 1, wherein the period of time is 60 minutes.

3. The waterless decarboxylation device of claim 1, comprising at least one second sensor configured to detect the temperature at a position within the waterless decarboxylation device at a distance from the sealed container.

4. The waterless decarboxylation device of claim 3, wherein the position comprises at least one of the sealed container, the foam layer, the bottom of the sealed container, and a space inside a canister base attached to the canister.

5. The waterless decarboxylation device of claim 1, further comprising a canister base attached to the foam layer.

6. The waterless decarboxylation device of claim 5, wherein the canister base comprises a button and/or a light.

7. The waterless *cannabis* decarboxylation device of claim 1, wherein the sealed container comprises a cylindrical shape.

8. The waterless *cannabis* decarboxylation device of claim 1, wherein the foam layer comprises an insulation layer.

* * * * *

UNITED STATES PATENT AND TRADEMARK OFFICE
CERTIFICATE OF CORRECTION

PATENT NO. : 10,710,038 B2
APPLICATION NO. : 15/756534
DATED : July 14, 2020
INVENTOR(S) : Shanel A. Lindsay Page 1 of 1

It is certified that error appears in the above-identified patent and that said Letters Patent is hereby corrected as shown below:

In the Claims

Column 14, Line 40, Claim 7, after "waterless" delete "cannabis"

Column 14, Line 43, Claim 8, after "waterless" delete "cannabis"

Signed and Sealed this
Twenty-ninth Day of September, 2020

Andrei Iancu
*Director of the United States Patent and Trademark Office*